United States Patent [19]
Bonitati et al.

[11] Patent Number: 5,586,821
[45] Date of Patent: Dec. 24, 1996

[54] BONE CEMENT PREPARATION KIT

[75] Inventors: John A. Bonitati; Kirt L. Case, both of Warsaw; Michael E. Hawkins, Columbia City; Stephen H. Hoag, Warsaw, all of Ind.

[73] Assignee: Zimmer, Inc., Warsaw, Ind.

[21] Appl. No.: 541,360

[22] Filed: Oct. 10, 1995

[51] Int. Cl.⁶ ............................................. B01F 13/06
[52] U.S. Cl. ..................... 366/139; 366/189; 366/332; 366/602
[58] Field of Search .................... 366/139, 602, 366/129, 130, 189, 190, 191, 255, 256, 332, 333

[56] References Cited

U.S. PATENT DOCUMENTS

| | | | |
|---|---|---|---|
| 4,575,255 | 3/1986 | Kafka | 366/343 |
| 4,721,390 | 1/1988 | Lidgren | 366/139 |
| 4,973,168 | 11/1990 | Chan | 366/139 |
| 5,100,241 | 3/1992 | Chan | 366/139 |
| 5,252,301 | 10/1993 | Nilson et al. | 422/225 |
| 5,328,262 | 7/1994 | Lidgren et al. | 366/139 |
| 5,395,167 | 3/1995 | Murray | 366/139 |

FOREIGN PATENT DOCUMENTS

| | | | |
|---|---|---|---|
| 2239818 | 7/1991 | United Kingdom | B65D 25/08 |
| WO90/13355 | 11/1990 | WIPO | B01F 3/12 |

OTHER PUBLICATIONS

MITAB, Mit Vac® Vacuum Mixing System (No Date).
Osteobond Vacuum Mixing Systems, Zimmer, Inc, 1991.
Porosity Reduction Technology, Mixing and Fume Evacuation Systems, Zimmer, Inc., 1995.
Zimmer® Vacuum Mixing System, Zimmer, Inc., 1986.

*Primary Examiner*—Robert W. Jenkins
*Attorney, Agent, or Firm*—Todd A. Dawson

[57] ABSTRACT

A preassembled collection of disposable mixing apparatus and constituent components needed for the vacuum mixing and preparation of bone cement and packaged as a single disposable kit is disclosed. The kit includes a contoured storage tray, ampules of liquid cement monomer, packets of powder cement copolymer, a small portable vacuum pump, connecting tubing with a vacuum indicator, a mixing cartridge, a cartridge cap and agitator, an assortment of connectable cement nozzles, and a funnel attachment. The kit can be packaged as a single unit for convenient and efficient use in the sterile environment of an operating room. The disposable telescoping mixing cartridge of the kit employs a telescoping mixing cartridge with a vacuum release mechanism.

16 Claims, 10 Drawing Sheets

BONE CEMENT PREPARATION KIT

This invention relates to a disposable preassembled collection of preparation apparatus and various cement components used in the preparation of bone cement. The collection of disposable apparatus and constituent components being packaged as a single sterile kit for convenience and includes a telescoping mixing cartridge with a vacuum release mechanism and a break-away agitator.

BACKGROUND OF THE INVENTION

In many orthopaedic surgical procedures, bone cements are used to fix implants to the bone. Conventional bone cements are generally polymeric materials, which are prepared by copolymerization of its components as needed. Bone cement is prepared by copolymerizing a liquid monomer and a powdered copolymer, such as methyl methacrylate and polymethyl methacrylate or methyl methacrylate-styrene. During mixing of the constituent components of the cement, air bubbles may be formed within the cement. It is thought that to improve the resultant strength of the cement, the air bubbles must be evacuated from the mixture to ensure a uniform reaction product. Consequently, the mixing of the constituent components is ideally performed in a vacuum.

The separate constituent components may be mixed within a mixing cartridge as is well known in the art. The mixing cartridge, when fully extended, provides a larger volume for mixing the constituent components to ensure that the constituent components are adequately mixed. Such mixing cartridges are generally enclosed by removable caps, which include a valved port for connection to a vacuum pump. Vacuum pumps draw a vacuum within the cartridges during the mixing process to reduce the occurences of air bubbles within the cement. The caps have an off-set outlet port through which the mixed cement compound is expelled and a central opening through which an agitator is reciprocally disposed. The agitator has an elongated shaft and a mixing paddle for mixing the constituent components. In a prior art vacuum cartridge mixing device, an end plunger is released after mixing yet while the cartridge is still under a vacuum. The vacuum pressure within the cartridge causes the plunger to be drawn into the cartridge to collect the cement. The plunger stops moving within the cartridge when the force exerted by the vacuum equalizes. After the cement is throughly mixed, the agitator shaft is broken off and the cartridge is inserted into a conventional cement applicator gun. Cement applicator guns are well known in the art. Generally, a variety of cement nozzles are affixed to the outlet port to aid in the application of the cement within the bone cavity. Because the outlet port is off center, a certain amount of cement cannot be expelled from the cartridge, and is discarded with the disposal of the cartridge.

Heretofore, the various cement constituent components and mixing apparatus have been individually packaged and provided to the user. Since the cement sets rapidly, the preparation and application of bone cement is time critical. Preparation of bone cement is generally performed in the sterile field of the operating room. Consequently, each piece of apparatus must be provided in a sterile package. Providing all of the various mixing apparatus and cement constituent components as a single preassembled collection or kit would be more convenient for the users in the operating room.

SUMMARY OF THE INVENTION

This invention provides a preassembled collection of disposable mixing apparatus and various cement constituent components needed for the preparation of bone cement in a convenient disposable kit. The kit includes a contoured storage tray, ampules of liquid cement monomer, packets of powder cement copolymer, a vacuum pump, connecting tubing with a vacuum indicator, a mixing cartridge, a cartridge cap and agitator, an assortment of connectable cement nozzles, and a funnel attachment. The kit can be packaged as a single unit for convenient and efficient use in the sterile environment of an operating room. In addition the contoured tray holds the various items in convenient positions to assist the user during the preparation of the bone cement. For example, the tray holds the mixing cartridge in a stable upright position so that the user does not have to hold the cartridge, leaving his hands free to operate the agitator or the vacuum pump.

The disposable telescoping mixing cartridge of the kit employs a vacuum release mechanism which releases the vacuum within the cement cartridge as the telescoping tubes are being compressed. The cartridge includes two telescoping tubular cylinders. The inner cylinder is shiftably received within the outer cylinder. The inner cylinder has an L-shaped longitudinal channel, and the outer cylinder includes a protrusion or key which is seated within the channel to provide for the lock and release of the inner cartridge relative to the outer cartridge. Alternatively, the channel may be stepped thereby allowing the inner cylinder to be rotated and axially moved within the outer cylinder between three selective positions: a fully extended mixing position, an intermediate vacuum release position, and a retracted applicator position.

The cartridge cap includes a break-away agitator, which allows a single opening to serve as both an outlet port for the cement and the opening through which the agitator is reciprocated. The agitator includes a handle and an elongated shaft reciprocally disposed within the outlet port of the cap. The shaft includes a tubular outer sleeve and an inner rod axially disposed within the sleeve. The sleeve has a fragible hollow distal end. Agitator paddles extend radially from the distal end of the sleeve for assisting in the mixing of the constituent components of the bone cement. The distal end of the rod terminates in an integral dumbbell shaped end plug. The small diameter of the middle segment of the dumbbell shaped end plug is positioned approximate to an annular notch formed in the sleeve. The distal end of the sleeve can be detached from the shaft so that the mixed cement compound can be expelled therethrough. The configuration of the dumbbell shaped end plug allows the rod to be bent at the middle section of the end plug while the sleeve is fractured at the notch. The hollow distal end of the sleeve remains seated within the outlet port of the cap to provide a passage for the mixed cement compound to be expelled.

Accordingly, an advantage of this invention is to provide collection of disposable mixing apparatus and cement constituent components for vacuum mixing and cartridge delivery in a single sterile kit for convenient use.

Another advantage of this invention is that the tray included in the kit holds the mixing cartridge while the constituent components are mixed so that the cartridge does not have to be manually supported during the preparation of the cement compound.

Another advantage of this invention is that the telescoping mixing cartridge has a vacuum release mechanism which releases the vacuum during collapsing of the telescoping cartridge.

Another advantage of this invention is that the cap includes a single outlet port through which the agitator is reciprocated during the mixing process and cement is expelled during cement application.

Other advantages will become apparent upon a reading of the following description.

BRIEF DESCRIPTION OF THE DRAWINGS

A preferred embodiment of the invention has been depicted for illustrative purposes only wherein.

DESCRIPTION OF THE PREFERRED EMBODIMENT

The preferred embodiments herein described are not intended to be exhaustive or to limit the invention to the precise forms disclosed. Rather, they are chosen and described to best explain the invention so that others skilled in the art might utilize their teachings.

Figure 1:
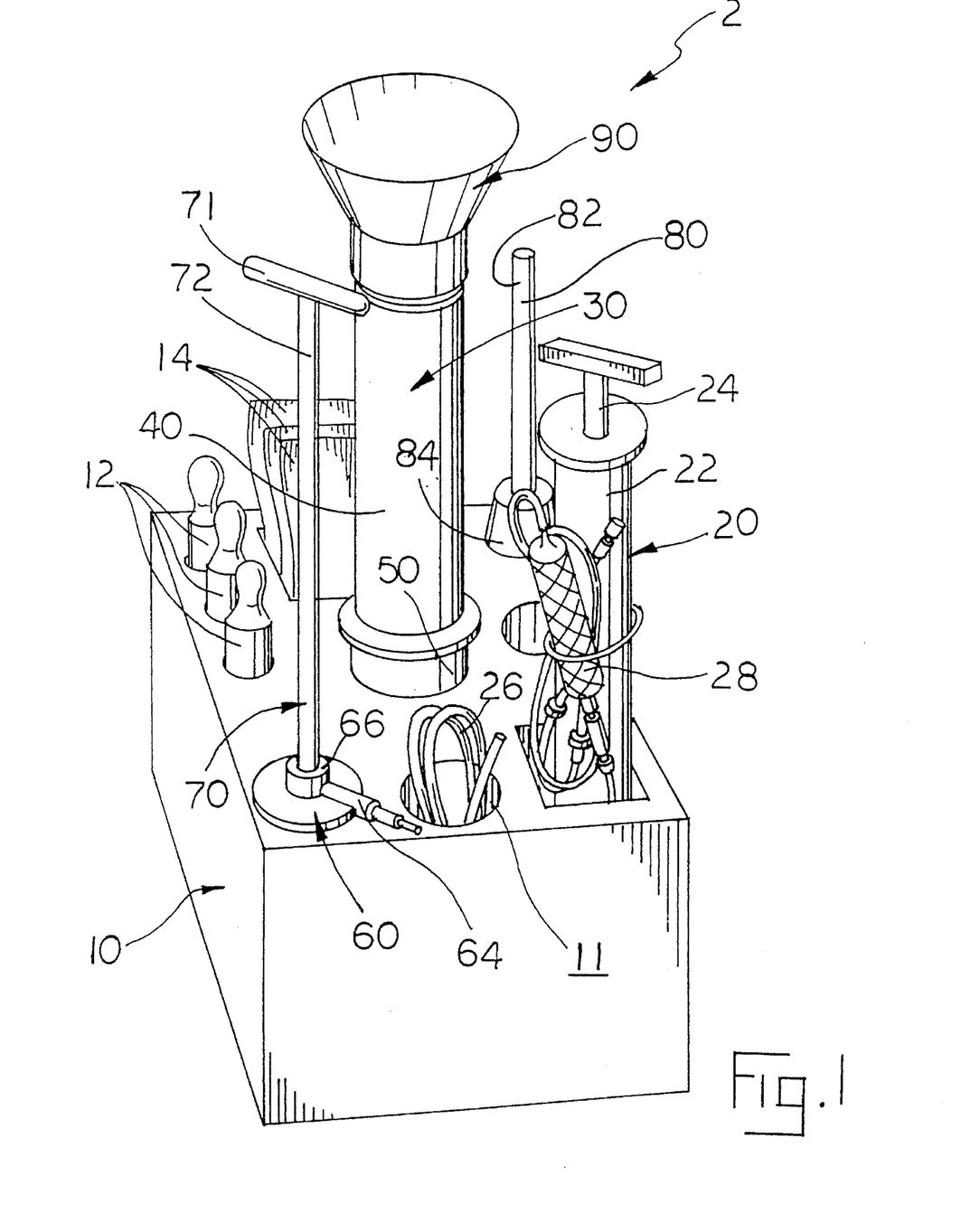
FIG. 1 is a perspective view of the kit of this invention.

FIG. 1 shows the collection of disposable hems of kit 2 of this invention for use in the preparation of bone cement. Kit 2 consists of the following items: a contoured storage tray 10, ampules 12 of liquid cement monomer, packets 14 of powdered cement polymer, vacuum pump 20, connecting tubing 26 having a vacuum indicator 28, a mixing cartridge 30, a cartridge cap 60 and break-away agitator 70, an assortment of connectable cement nozzles 80, and a funnel attachment 90. Preferably, tray 10 is constructed from a molded plastic, which has a plurality of contoured recesses 11 (FIGS. 1, 8 and 9) within which the various mixing apparatus and constituent components 4 of the cements are stored. As shown in FIG. 1, tray 10 allows all of the kit hems to be stored and packaged in a single sterile covering (not shown). Each of the kit items are held in their individual contoured recesses 11 formed in tray 10. In addition, tray 10 holds the various items at a convenient position to assist the user in preparing the bone cement. For example, tray 10 holds mixing cartridge 30 in a stable upright position so that the user does not have to hold the cartridge, leaving his hands free to pour in the constituent components, operate vacuum pump 20, or agitator 70.

Preferably, the constituent components 4 of the cements are individually packaged in premetered portions. The liquid monomer components are provided in ampules 12 and the powder copolymers are provided in sealed packets 14, although any suitable packaging for the components may be provided with the kit of this invention. Ampules 12 of the liquid monomer and packets 14 of powder copolymer are well known in the art and are commercially available from a variety of sources. Vacuum pump 20 uses a reciprocated piston design, although any suitable vacuum pump may be included as pan of kit 2. Vacuum pump 20 includes a cylindrical body 22 and reciprocating shaft 24, which drives an internal piston (not shown). Vacuum pump 20 also includes a check valve (not shown) to permit air flow in one direction only through the pump orafice. The length of tubing 26 is used to connect pump 20 to cap 60 when connected to mixing cartridge 30. Preferably tubing 26 includes vacuum indicator 28. Vacuum indicator 28 is a plastic or rubber bulb, which collapses under the negative pressure of the vacuum drawn by pump 20.

Mixing cartridge 30 is preferably constructed of a disposable semi-transparent plastic, which allows the admixture of the constituent components 4 to be viewed. Cartridge 30 includes two telescoping tubular cylinders 40, 50. Both cylinders 40, 50 have open proximal and distal ends. Outer cylinder 40 axially receives inner cylinder 50 in a telescoping configuration. The outer diameter of inner cylinder 50 is concentrically seated against the inner diameter of outer cylinder 40. The outer peripheral surface of inner cylinder 50 is in a tight but not hermetically sealed engagement with the inner peripheral surface of outer cylinder 50 in a piston like manner. An air impermeable piston plug 32 is disposed within inner cylinder 50 approximate its distal end, so as to close the distal end of inner cylinder 50. Plug 32 is axially slidable within inner cylinder 50 for expelling the mixed cement compound 6 from cartridge 30 when the cartridge is connected to a cement gun.

Figure 2:
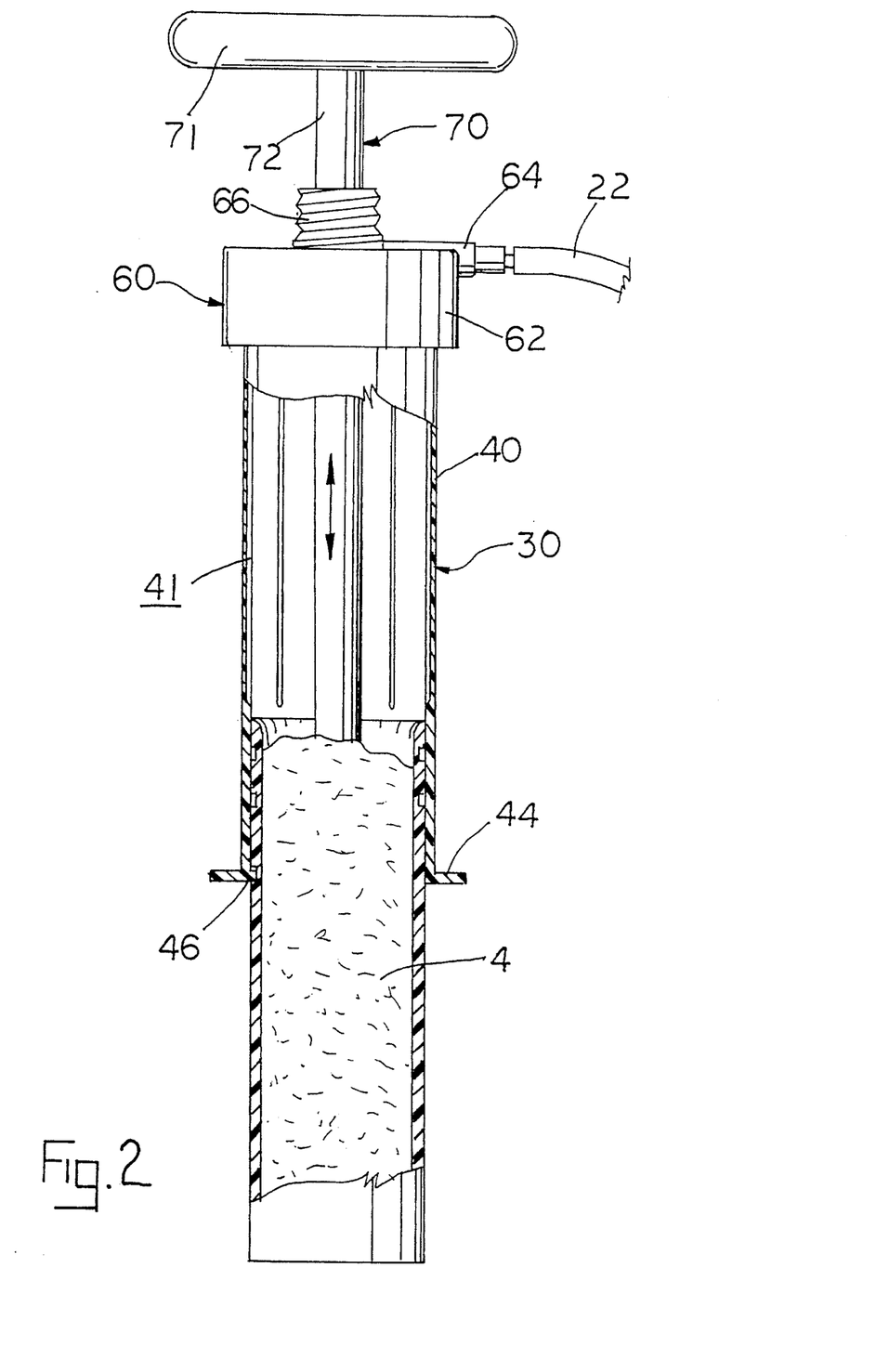
FIG. 2 is a side view of the mixing cartridge and the connected cap with a portion cut away to illustrate the mixing of the constituent components.
Figure 5:
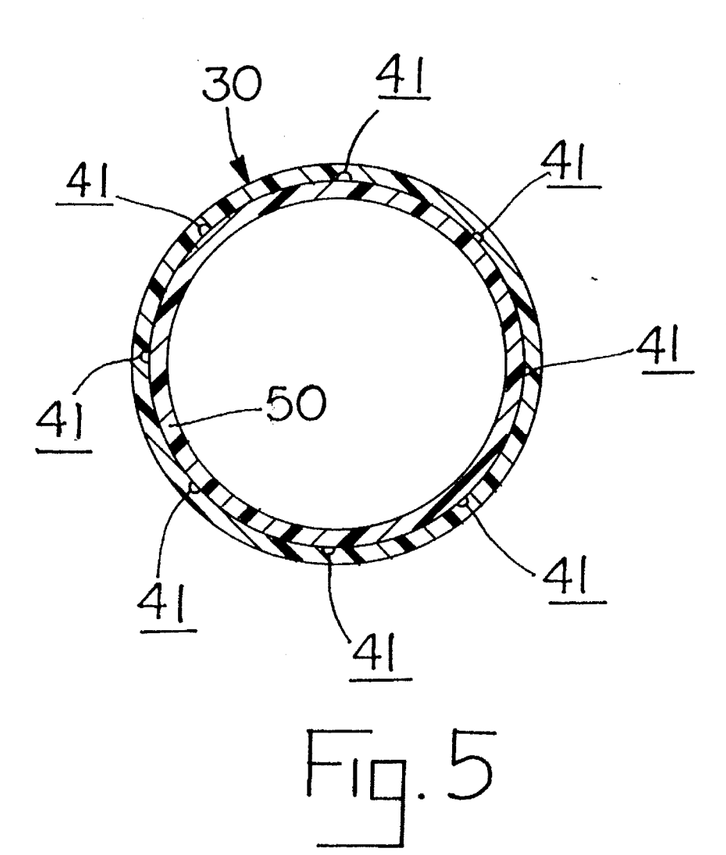
FIG. 5 is a sectional view of the mixing cartridge taken along line 5—5 of FIG. 3.

Outer cylinder 40 includes a threaded outer rim 42 adjacent its open proximal end. Threaded rim 42 allows connection of cap 60 and funnel attachment 90 to cartridge 30. While outer cylinder 40 is shown herein as including an outer thread rim, any suitable connection structure can be employed to provide the connection to funnel attachment and cap 60. Outer cylinder 40 also includes an annular end flange 44, which extends outwardly approximate its open distal end, and a block protrusion or key 46, which protrudes inwardly. As shown in FIGS. 2 and 5, the inner surface of outer cylinder 40 has a plurality of pressure evacuation grooves 41, which extend longitudinally from its proximal end.

Figure 3:
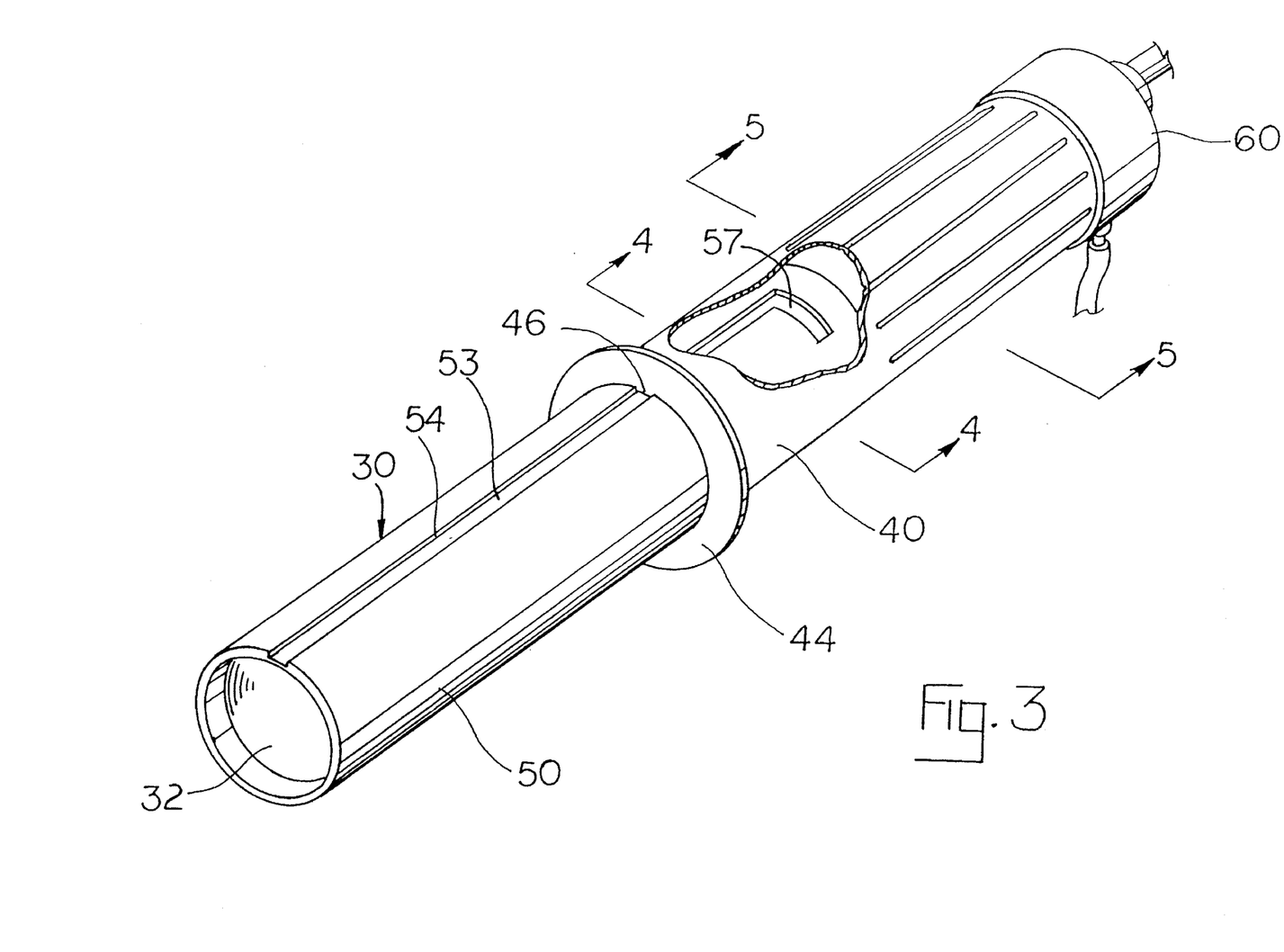
FIG. 3 is a perspective view of the mixing cartridge of this invention with a portion cut away to illustrate its vacuum release mechanism.
Figure 10:
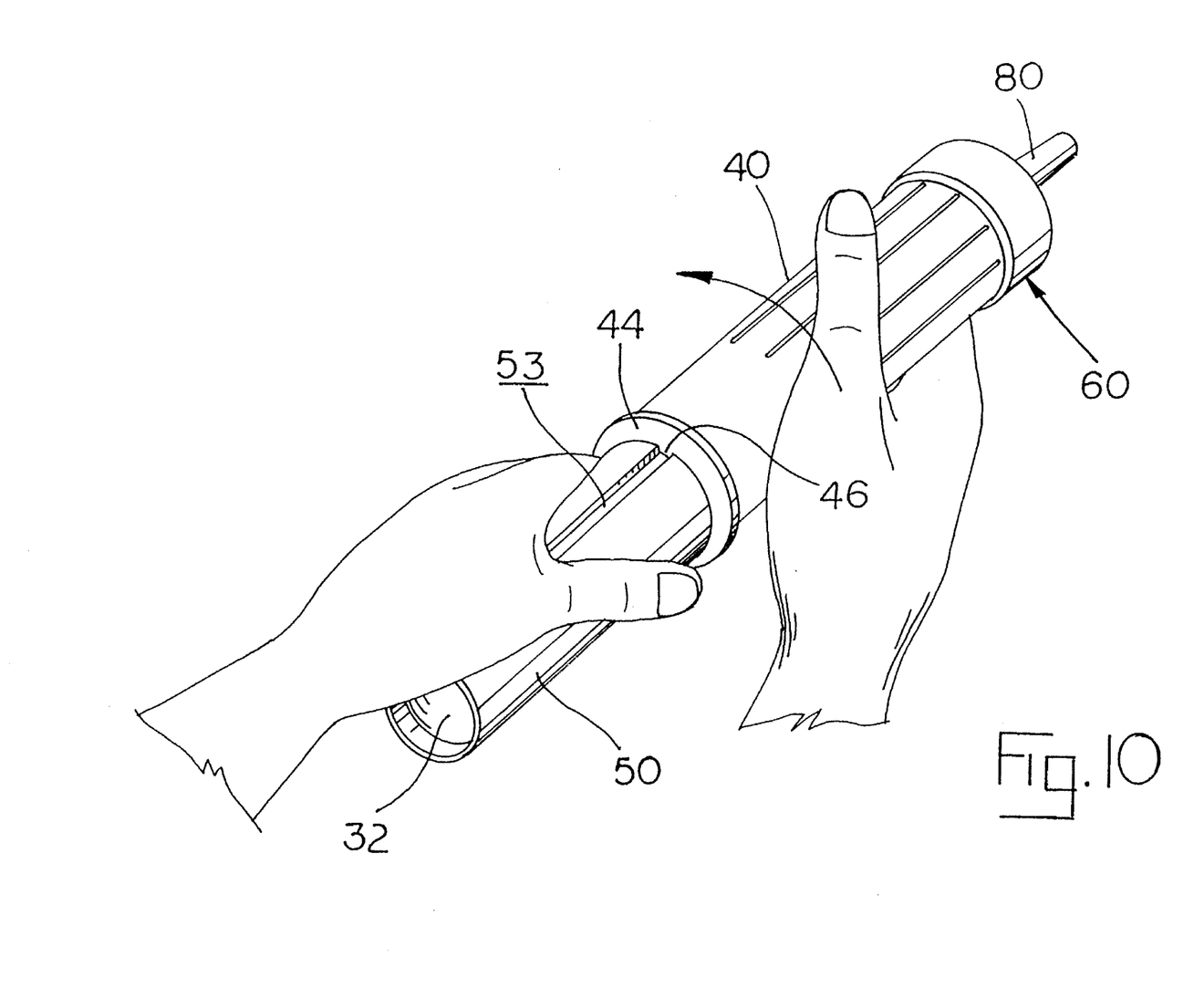
FIG. 10 is a perspective view of the mixing cartridge of this invention showing the manipulation of the inner cylinder within the outer cylinder to release the vacuum pressure and to collapse the cartridge.
Figure 11:
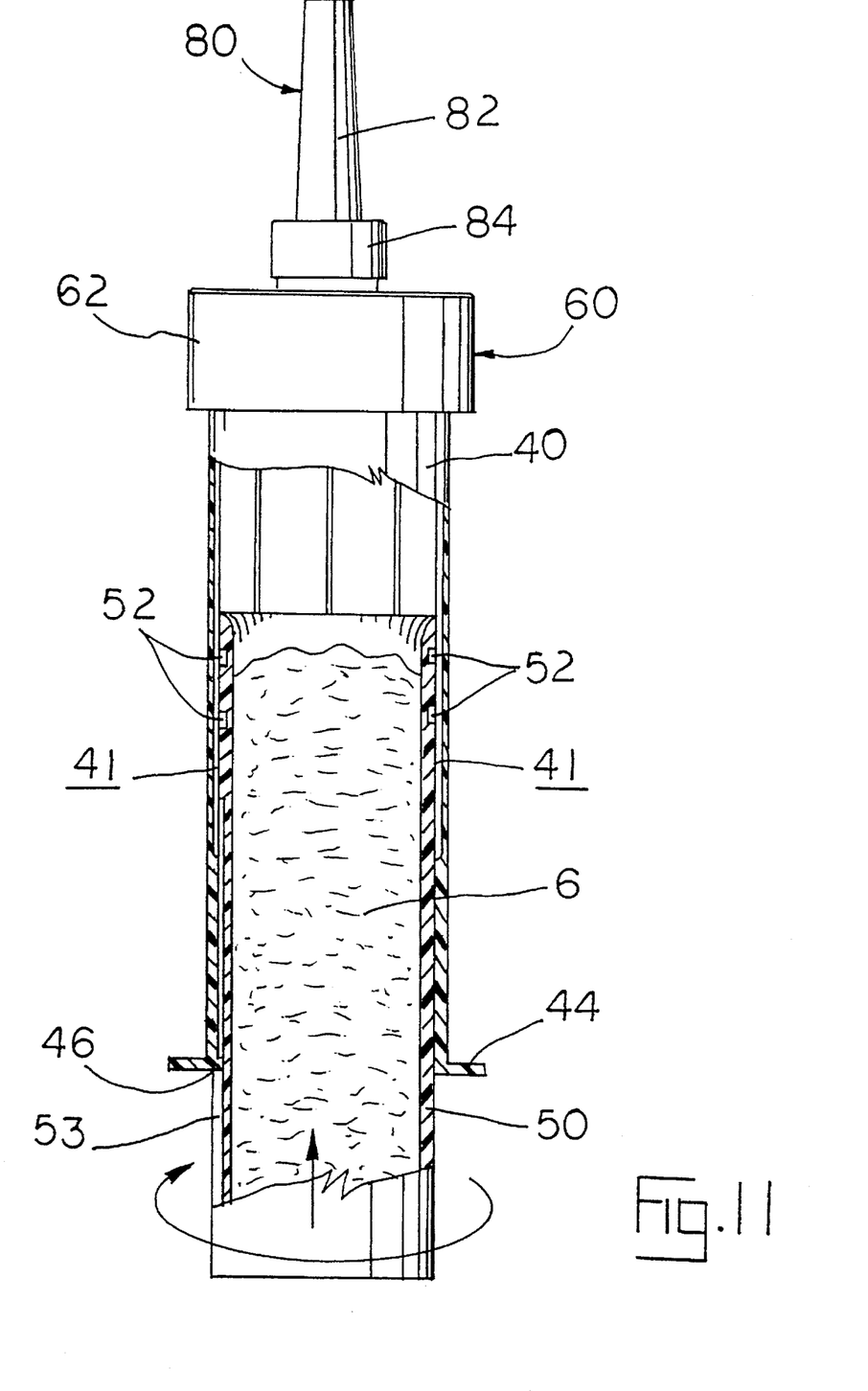
FIG. 11 is a side view of the mixing cartridge of this invention and a connected cement nozzle with a portion cut away to show the position of the inner and outer cylinders.

Inner cylinder 50 includes a pair of O-rings 52, which are seated within annual grooves 51 formed approximate its proximal end. O-rings 52 provide a hermetic seal between cylinders 40, 50. As shown in FIG. 3, inner cylinder 50 has an L-shaped longitudinal channel 53. Channel 53 includes a short lateral section 57 which connects to a major longitudinal section 54. The L-shaped channel allows the inner cylinder 50 to be rotationally and axially movable between two positions: a fully extended mixing position wherein key 46 is seated within lateral section 57, and a vacuum release and retracted postion wherein the key is accommodated within the major longitudinal section. As shown in FIGS. 3, 10 and 11, key 46 of outer cylinder 40 is seated within channel 53 of inner cylinder 50. In an alternative embodiment, illustrated in FIG. 3A, the channel 53' is formed in a stepped configuration and includes a short intermediate lateral section 55', which connects the major longitudinal section 54' to the minor longitudinal section 56 and a short lateral end section 57'. Stepped channel 53' and key 46 provide a two stage vacuum release mechanism for cartridge 30. Stepped channel 53' allows inner cylinder 50 to be rotationally and axially moved between three positions: a fully extended mixing position, an intermediate vacuum release position, and a retracted applicator position.

Figure 6:
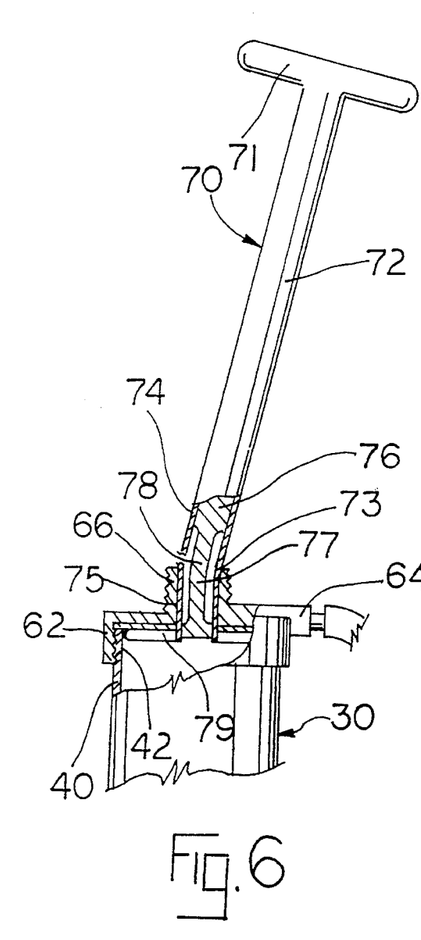
FIG. 6 is a sectional view of the cap and breakaway agitator of this invention showing the dumbbell shaped end plug of the rod bent to sever the distal end of the outer sleeve.
Figure 7:
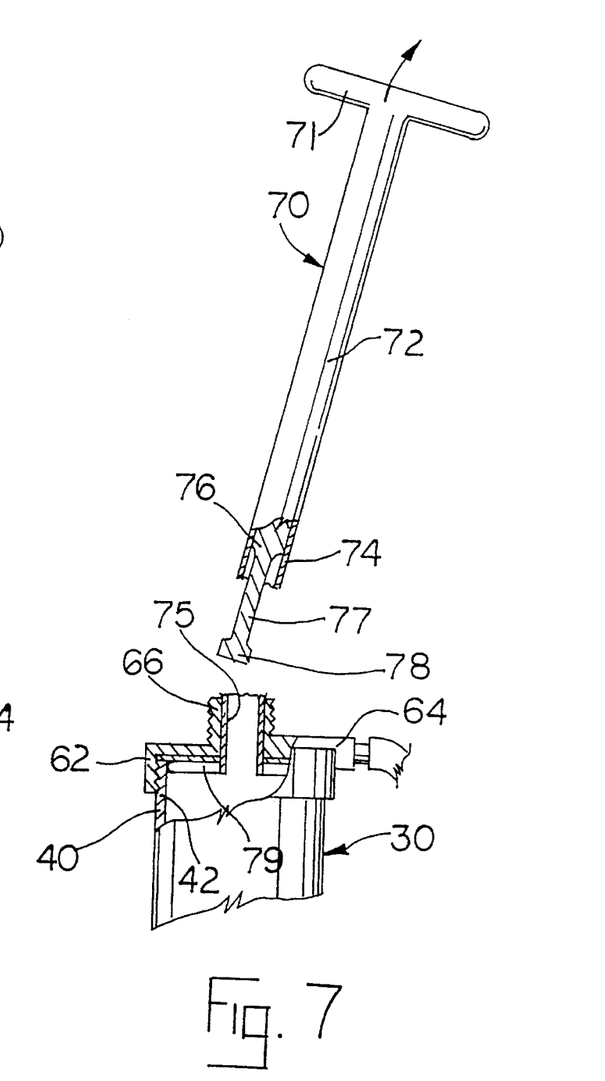
FIG. 7 is a sectional view of the cap and breakaway agitator of this invention showing the shaft and dumb bell shaped end plug withdrawn from the distal end of the sleeve.

As shown in FIGS. 2, 6 and 7, cartridge cap 60 includes an annular rim 62. The inner surface (not shown) of rim 62 is threaded to mate with the threaded rim 42 of outer cylinder 40 to provide a hermetically sealed connection over the proximal end of outer cylinder 40. Cap 60 includes a one way valve port 64, which is connectable to vacuum pump 20. Cap 60 includes a centered cement outlet port 66. The outer surface of cement port 66 is threaded to allow connection of cement nozzles 80 to cap 60.

As shown in FIGS. 6 and 7, agitator 70 includes a handle 71 and an elongated shaft 72 reciprocally disposed within outlet port 66 of cap 60. Shaft 72 includes a tubular outer sleeve 74 and an inner rod 76 axially disposed within sleeve 74. Shaft sleeve 74 is fragible and has a detachable distal end 75. Agitator paddles 79 extend radially from distal end 75 of shaft sleeve 74 for assisting in the mixing of the constituent components 4 of the bone cement. The distal end of rod 76 terminates in an integral dumbbell shaped end plug 78. The small diameter of the middle segment 77 of dumbbell shaped end plug 78 is positioned approximate to an annular notch 73 formed in shaft sleeve 74. As shown in FIGS. 6 and 7, distal end 75 of sleeve 74 can be detached from shaft 72 so that the mixed cement compound 6 can be expelled therethrough. When shaft 72 is withdrawn to its outer extreme from cartridge 30, paddles 79 abut against the inner wall of cap 60 and distal end 75 of sleeve 72 is fitted within outlet port 66 of cap 60. The configuration of dumbbell shaped end plug 78 allows rod 76 to be bent at middle section 77 of end plug 78 while sleeve 74 is fractured at notch 73. The hollow distal end 75 of sleeve 74 remains within outlet port 66 of cap 60 to provide a passage for the mixed cement compound 6 to be expelled.

Figure 8:
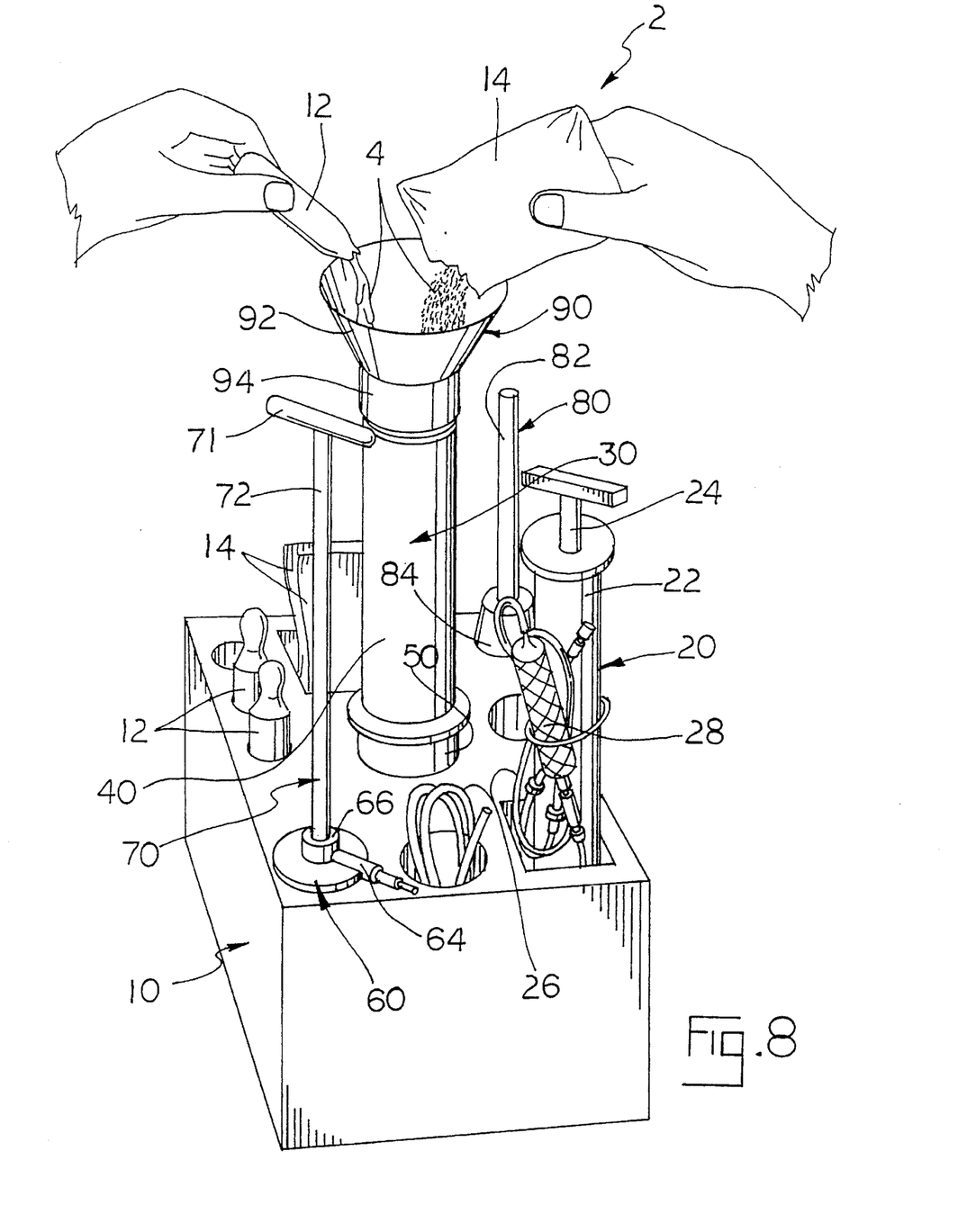
FIG. 8 is a perspective view of the kit of this invention showing the liquid and powder constituent components being poured into the mixing cartridge through a funnel attachment connected to the cartridge.

As shown in FIGS. 1, 10 and 11, cement nozzles 80 are of conventional design and include an elongated neck 82 and a coupling part, which is adapted to be fitted to outlet port 66 of cap 60. As shown in FIGS. 1 and 8, funnel attachment 90 includes a conical flange 92 and an annular neck 94. Neck 94 has a threaded inner surface (not shown), which allows the funnel to be connected to the proximal end of cartridge 30.

Figure 9:
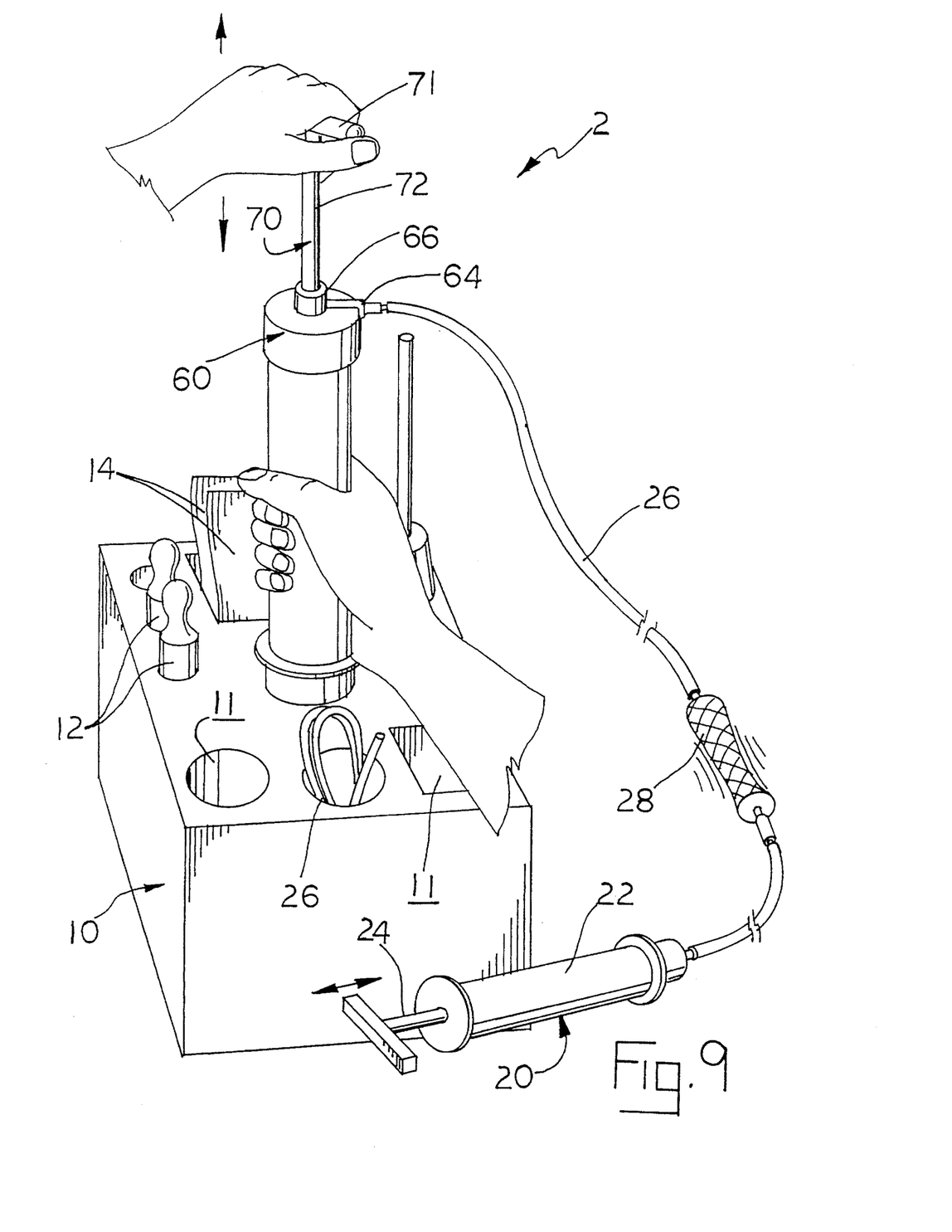
FIG. 9 is a perspective view of the kit of this invention showing the cap connected to the mixing cartridge for facilitating mixing of the constituent components and the vacuum pump connected to the cap for drawing a vacuum in the cartridge.

FIGS. 8–11 demonstrate the use of kit 2 in the preparation of bone cement. Kit 2 is packaged in an external packaging (not shown) with funnel attachment 90 connected to cartridge 30. One will notice that cartridge 30 is packaged in tray 10 in its extended mixing position for the convenience of the user. As shown in FIG. 8, the cement constituent components 4 of the cement are poured into mixing cylinder 30 through funnel 90. Once the proper volumes of the various constituent components 4 of the cement have been poured into the cartridge, funnel attachment 90 is removed and discarded. Cap 60 is then removed from tray 10 and attached to cartridge 30. Vacuum pump 20, tubing 22, and vacuum indicator 24 are also removed from tray 10 and connected to vacuum port 64 of cap 60. Once cap 60 and vacuum pump 20 are connected to cartridge 30 as shown in FIG. 9, a vacuum is drawn within cartridge 30 by manually reciprocating shaft 24 of vacuum pump 20. Vacuum indicator 28 collapses to indicate that the cartridge is at the desired vacuum pressure. The vacuum pump may then be removed and the vacuum is maintained by a one-way check valve (not shown) within cap 60. The constituent components 4 of the cement are then mixed by manually reciprocating agitator 70 in a manner well know in the art. When the constituent components 4 of the cement have been thoroughly mixed, agitator part 70 is pulled to its outer limit so that agitator paddles 79 abut against cap 60.

As shown in FIGS. 10 and 11, the vacuum pressure within cartridge 30 is then released and cartridge 30 is compressed for use in a cement injector gun (not shown). To release the vacuum pressure within cartridge 30, inner cylinder 50 is rotated and axially compressed within outer cylinder 40 from its extended position to its intermediate vacuum release position. Inner cylinder 50 is rotated within outer cylinder 40 to move key 46 through lateral end section 57 into longitudinal section 54 so that the inner cylinder can be compressed. With key 46 aligned with section 57, the inner cartridge is in its vacuum release and collapsing position. In the vacuum release position, the position of inner cylinder 50 within outer cylinder 40 locates O-rings 52, which provide the hermetic seal between the inner and outer cylinder 40, 50, between the opposed ends of grooves 41 formed in the outer cylinder 40. Grooves 41 provide an air passage into the interior of cartridge 30 around O-rings 52 through channels 41.

Figure 3A:
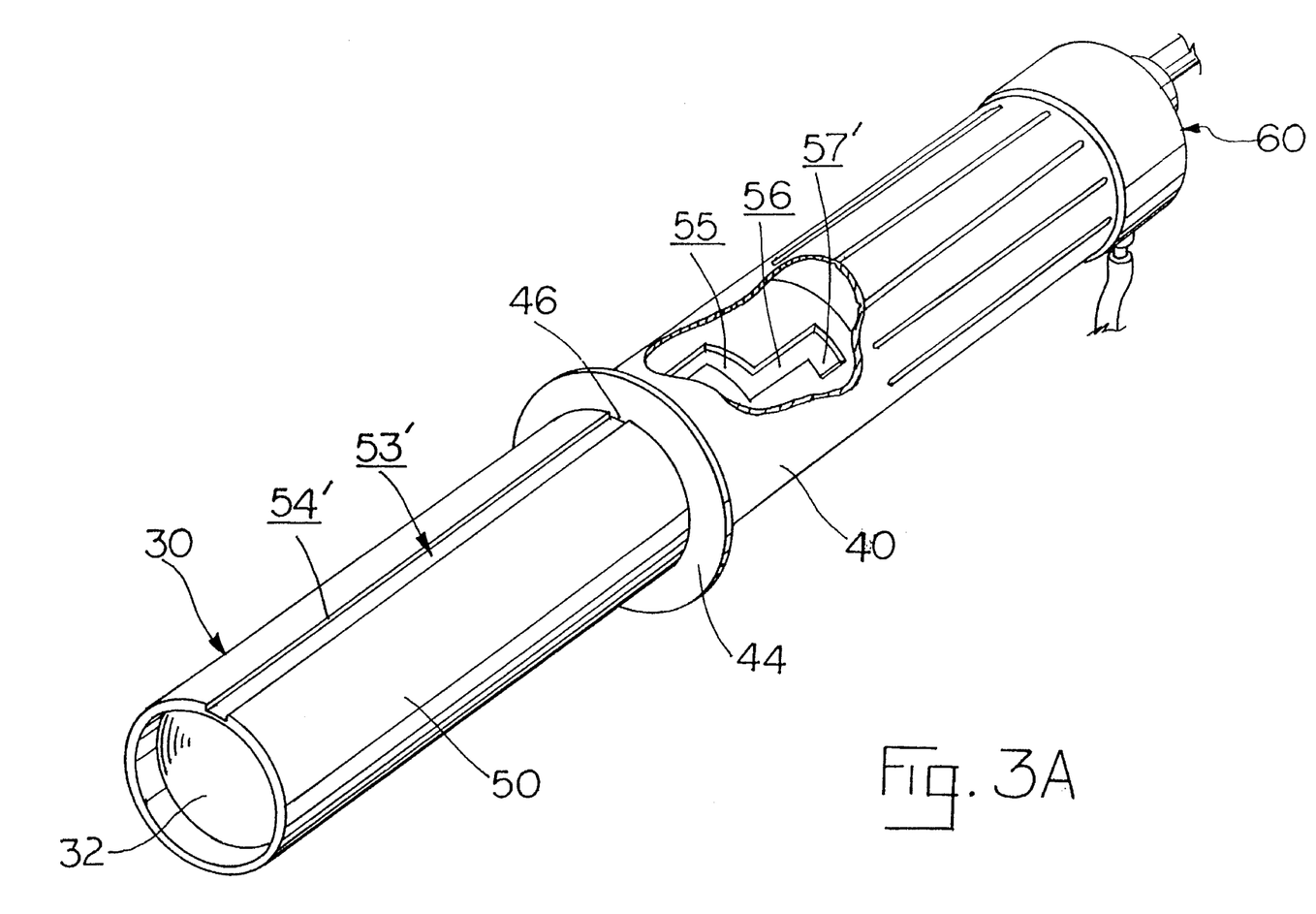
FIG. 3A is a perspective view of the mixing cartridge of this invention with a portion cut away to illustrate its two stage vacuum release mechanism.
Figure 4:
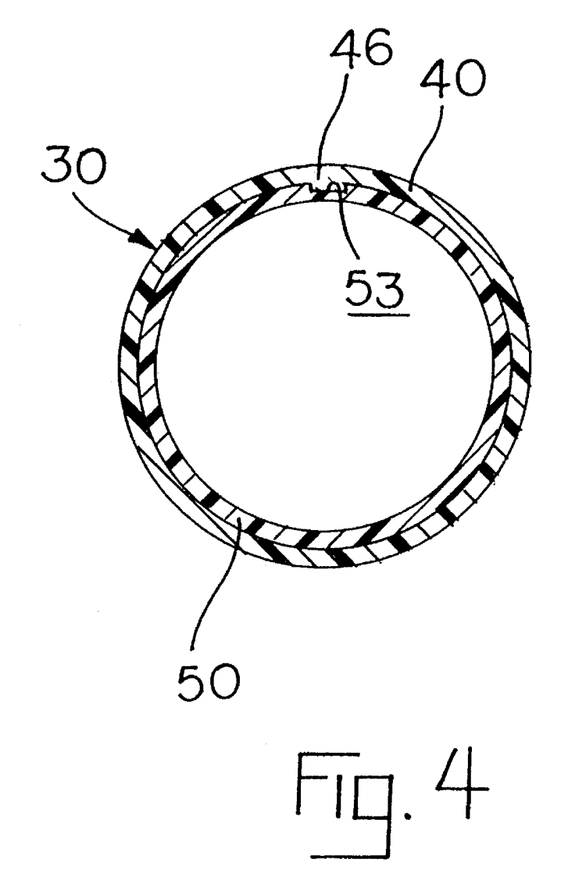
FIG. 4 is a sectional view of the mixing cartridge taken along line 4—4 of FIG. 3.

To release the vacuum pressure within cartridge 30 in the alternative embodiment of FIG. 3A, inner cylinder 50 is rotated and axially compressed within outer cylinder 40 from its extended position to its intermediate vacuum release position. Inner cylinder 50 is rotated within outer cylinder 40 to move key 46 through lateral end section 57 into longitudinal section 56 so that the inner cylinder can be compressed. The axial compression of inner cylinder 50 within outer cylinder 40 is arrested at its intermediate vacuum release position when key 46 reaches intermediate lateral section 55. In the vacuum release position, the position of inner cylinder 50 within outer cylinder 40 locates O-rings 52, which provide the hermetic seal between the inner and outer cylinder 40, 50, between the opposed ends of grooves 41 formed in the outer cylinder 40. Grooves 41 provide an air passage into the interior of cartridge 30 around O-rings 52 through channels 41. Once the pressure within cartridge 30 has been equalized, inner cylinder 40 is rotated again to move key 46 along lateral intermediate section 55 into longitudinal section 54. Now inner cylinder 50 can be completely compressed into outer cylinder 40 to its retracted position.

Once cartridge 30 is compressed into its retracted position, distal end 75 of sleeve 74 of the agitator is broken off and discarded as shown in FIGS. 6 and 7. When agitator 70 is broken off, plug 78 is pulled from the cap and outlet port 66 is opened. The suitable cement nozzle 80 can now be affixed to outlet port 66, and cartridge 30 inserted into the applicator gun (not shown).

It is understood that the above description does not limit the invention to the details given, but may be modified within the scope of the following claims.

I claim:

1. An apparatus for manufacturing bone cement by mixing a plurality of constituent components comprising:

a telecsoping cartridge including a tubular outer cylinder having an open proximal end and a distal end, and a tubular inner cylinder having an open proximal end and a distal end shiftably received within said outer cylinder distal end, said inner cylinder being axially extensible between an extended position, an intermediate position, and a retracted position, a cap connectable to said outer cylinder proximal end, said cap part including means for connecting said cartridge to a vacuum pump to draw a vacuum within said cartridge when said inner cylinder is in its said extended position, an end plug, shiftably disposed within said inner cylinder for axial movement within said inner cylinder towards said cap to expel said cement from said cartridge, and means for releasing vacuum pressure within said cartridge when said inner cylinder is in its said intermediate position.

2. The apparatus of claim 1 wherein said cartridge includes sealing means for hermetically sealing the shiftable engagement between the facing surfaces of said inner cylinder and said outer cylinder when said inner cylinder is in its said extended position.

3. The apparatus of claim 2 wherein said vacuum release means includes an elongated groove longitudinally defined in said facing surface of said outer cylinder, said sealing means being positioned between the opposed ends of said grooves.

4. The apparatus of claim 1 wherein said inner cylinder has a channel, the outer cylinder includes a key seated within said channel for longitudinal movement along the channel.

5. The apparatus of claim 4 wherein the channel formed in the inner cylinder has a stepped configuration defined by a first and second longitudinal section integrally connected by an intermediate lateral section and a lateral end section integrally connected to said second longitudinal section opposite said intermediate lateral section, said key seated within said lateral end section when said inner cylinder is in its extended position, said key seated within said intermediate lateral section when said cylinder is in its said intermediate position.

6. A collection of disposable apparatus and materials for manufacturing bone cement by mixing a plurality of constituent components comprising:

constituent components of said bone cement, a disposable mixing cartridge for mixing said constituent components therein, a disposable vacuum pump connectable to said cartridge for drawing a vacuum within said cartridge when said liquid and solid constituent components are mixed, and a disposable tray for supporting said liquid and solid constituent components packets, said mixing cartridge, and said vacuum pump to facilitate convenient mixing of cement.

7. The collection of claim 6 and a funnel attachment connectable to said cartridge.

8. The collection of claim 6 and cement nozzles connectable to said mixing cartridge.

9. A collection of disposable apparatus and materials for manufacturing bone cement by mixing a plurality of constituent components comprising:

constituent components of said bone cement, a disposable mixing cartridge for mixing said constituent components therein, a disposable vacuum pump connectable to said cartridge for drawing a vacuum within said cartridge when said liquid and solid constituent components are mixed and a disposable tray for supporting said liquid and solid constituent components packets, said mixing cartridge, and said vacuum pump to facilitate convenient mixing of cement, said cartridge includes a tubular outer cylinder having an open proximal end and a distal end, and a tubular inner cylinder having an open proximal end shiftably received within said outer cylinder distal end, said inner cylinder being axially extensible between an extended position, an intermediate position, and a retracted position, a cap connectable to said outer cylinder proximal end, said cap part including means for connecting said cartridge to a vacuum pump to draw a vacuum within said cartridge when said inner cylinder is in its said extended position, an end plug, shiftably disposed within said inner cylinder for axial movement within said inner cylinder towards said end to expel said cement from said cartridge, means for releasing vacuum pressure within said cartridge when said inner cylinder is in its said intermediate position.

10. The apparatus of claim 9 wherein said cartridge includes sealing means for hermetically sealing the shiftable engagement between the facing surfaces of said inner cylinder and said outer cylinder when said inner cylinder is in its said extended position.

11. The apparatus of claim 10 wherein said vacuum release means includes an elongated groove longitudinally defined in said facing surface of said outer cylinder, said sealing means being positioned between the opposed ends of said grooves.

12. The apparatus of claim 9 wherein said outer cylinder has a stepped channel defined therein, said other cylinder includes a key seated within said channel for longitudinal movement along its length.

13. The apparatus of claim 12 wherein said stepped channel being defined by a first and second longitudinal section integrally connected by an intermediate lateral section and a lateral end section integrally connected to said second longitudinal section opposite said intermediate lateral section, said key seated within said lateral end section when said inner cylinder is in its extended position, said key seated within said intermediate lateral section when said cylinder is in its said intermediate position.

14. A kit of non-reusable apparatus and materials for manufacturing bone cement by mixing a plurality of components comprising:

constituent components of said bone cement, a mixing cartridge for mixing said constituent components therein, a vacuum pump connectable to said cartridge for drawing a vacuum within said cartridge when said liquid and solid constituent components are mixed, and a tray for supporting said liquid and solid constituent components packets, said mixing cartridge, and said vacuum pump to facilitate convenient mixing of cement.

15. The kit of claim 14 and a funnel connectable to said cartridge to facilitate pouring the constituent components into the cartridge for mixing.

16. The kit of claim 14 and nozzles connectable to said mixing cartridge for ejecting the manufactured bone cement after mixing.

* * * * *